(12) United States Patent
Rozners et al.

(10) Patent No.: US 10,385,100 B2
(45) Date of Patent: Aug. 20, 2019

(54) COMPOSITIONS AND METHODS FOR RECOGNITION OF RNA USING TRIPLE HELIX FORMING PEPTIDE NUCLEIC ACIDS

(71) Applicant: The Research Foundation for The State University of New York, Binghamton, NY (US)

(72) Inventors: Eriks Rozners, Binghamton, NY (US); Thomas Zengeya, Frederick, MD (US)

(73) Assignee: The Research Foundation for the State University o, Binghamton, NY (US)

(*) Notice: Subject to any disclaimer, the term of this patent is extended or adjusted under 35 U.S.C. 154(b) by 330 days.

(21) Appl. No.: 15/221,021

(22) Filed: Jul. 27, 2016

(65) Prior Publication Data

US 2017/0009280 A1   Jan. 12, 2017

Related U.S. Application Data

(62) Division of application No. 14/066,006, filed on Oct. 29, 2013, now Pat. No. 10,260,089.

(60) Provisional application No. 61/719,691, filed on Oct. 29, 2012.

(51) Int. Cl.
   *C07H 21/00* (2006.01)
   *C07K 14/00* (2006.01)
   *C12Q 1/6839* (2018.01)
   *C07K 7/08* (2006.01)
   *C07K 9/00* (2006.01)

(52) U.S. Cl.
   CPC .............. *C07K 14/003* (2013.01); *C07K 7/08* (2013.01); *C07K 9/00* (2013.01); *C12Q 1/6839* (2013.01)

(58) Field of Classification Search
   CPC .................................................. C07K 14/003
   USPC ....................................................... 536/23.1
   See application file for complete search history.

(56) References Cited

U.S. PATENT DOCUMENTS

2011/0152346 A1* 6/2011 Karleson ............... C12N 15/111
                                                                 514/44 A

* cited by examiner

*Primary Examiner* — Jezia Riley
(74) *Attorney, Agent, or Firm* — Tully Rinckey PLLC; Steven M. Hoffberg

(57) ABSTRACT

Peptide nucleic acids containing thymidine and 2-aminopyridine (M) nucleobases formed stable and sequence selective triple helices with double stranded RNA at physiologically relevant conditions. The M-modified PNA displayed unique RNA selectivity by having two orders of magnitude higher affinity for the double stranded RNAs than for the same DNA sequences. Preliminary results suggested that nucleobase-modified PNA could bind and recognize double helical precursors of microRNAs.

19 Claims, 4 Drawing Sheets

Specification includes a Sequence Listing.

SEQUENCE LISTING

<160> NUMBER OF SEQ ID NOS: 14

<210> SEQ ID NO 1
<211> LENGTH: 12
<212> TYPE: DNA
<213> ORGANISM: Artificial Sequence
<220> FEATURE:
<223> OTHER INFORMATION: PNA1, 3' Lys-NH-, 5' -CONH2

<400> SEQUENCE: 1
tcttcttctt tc                                                          12

<210> SEQ ID NO 2
<211> LENGTH: 10
<212> TYPE: RNA
<213> ORGANISM: Artificial Sequence
<220> FEATURE:
<223> OTHER INFORMATION: Triplex recognition site

<400> SEQUENCE: 2
gugauagggg                                                             10

<210> SEQ ID NO 3
<211> LENGTH: 28
<212> TYPE: RNA
<213> ORGANISM: Artificial Sequence
<220> FEATURE:
<223> OTHER INFORMATION: HRPA

<400> SEQUENCE: 3
gaaagaagaa gauuuucuu cuucuuuc                                          28

<210> SEQ ID NO 4
<211> LENGTH: 28
<212> TYPE: DNA
<213> ORGANISM: Artificial Sequence
<220> FEATURE:
<223> OTHER INFORMATION: DNAA

<400> SEQUENCE: 4
gaaagaagaa gattttctt cttctttc                                          28

<210> SEQ ID NO 5
<211> LENGTH: 28
<212> TYPE: RNA

-continued

```
<213> ORGANISM: Artificial Sequence
<220> FEATURE:
<223> OTHER INFORMATION: HRP1

<400> SEQUENCE: 5
ggagaggagg gauuuuccc uccucucc                                        28

<210> SEQ ID NO 6
<211> LENGTH: 28
<212> TYPE: RNA
<213> ORGANISM: Artificial Sequence
<220> FEATURE:
<223> OTHER INFORMATION: HRP2

<400> SEQUENCE: 6
ggagagaagg gauuuuccc uucucucc                                        28

<210> SEQ ID NO 7
<211> LENGTH: 28
<212> TYPE: RNA
<213> ORGANISM: Artificial Sequence
<220> FEATURE:
<223> OTHER INFORMATION: HRP3

<400> SEQUENCE: 7
ggagagcagg gauuuuccc ugcucucc                                        28

<210> SEQ ID NO 8
<211> LENGTH: 28
<212> TYPE: RNA
<213> ORGANISM: Artificial Sequence
<220> FEATURE:
<223> OTHER INFORMATION: HRP4

<400> SEQUENCE: 8
ggagaguagg gauuuuccc uacucucc                                        28

<210> SEQ ID NO 9
<211> LENGTH: 28
<212> TYPE: DNA
<213> ORGANISM: Artificial Sequence
<220> FEATURE:
<223> OTHER INFORMATION: HRP5

<400> SEQUENCE: 9
ggagaggagg gatttttccc tcctctcc                                       28

<210> SEQ ID NO 10
<211> LENGTH: 32
<212> TYPE: RNA
<213> ORGANISM: Artificial Sequence
<220> FEATURE:
<223> OTHER INFORMATION: HRP6

<400> SEQUENCE: 10
cacaggaaaa ugacuucggc caauauucug ug                                  32

<210> SEQ ID NO 11
<211> LENGTH: 28
<212> TYPE: DNA
<213> ORGANISM: Artificial Sequence
<220> FEATURE:
<223> OTHER INFORMATION: DNA analog of HRP2
```

```
<400> SEQUENCE: 11
ggagagaagg gatttttccc ttctctcc                                      28

<210> SEQ ID NO 12
<211> LENGTH: 31
<212> TYPE: RNA
<213> ORGANISM: Artificial Sequence
<220> FEATURE:
<223> OTHER INFORMATION: HRP6

<400> SEQUENCE: 12
ggugauaggg guucuucgga acuccuacac c                                  31

<210> SEQ ID NO 13
<211> LENGTH: 35
<212> TYPE: RNA
<213> ORGANISM: Artificial Sequence
<220> FEATURE:
<223> OTHER INFORMATION: HRP5

<400> SEQUENCE: 13
cgucgcuacu accacuucgg uggaaguaaa agucg                              35

<210> SEQ ID NO 14
<211> LENGTH: 33
<212> TYPE: RNA
<213> ORGANISM: Artificial Sequence
<220> FEATURE:
<223> OTHER INFORMATION: HRP6

<400> SEQUENCE: 14
cgucacguca ugacuucggu ugggacgaag ucg                                33
```

COMPOSITIONS AND METHODS FOR RECOGNITION OF RNA USING TRIPLE HELIX FORMING PEPTIDE NUCLEIC ACIDS

CROSS REFERENCE TO RELATED APPLICATION

The present application is a Division of U.S. patent application Ser. No. 14/066,006, filed Oct. 29, 2013, which is a non-provisional of, and claims benefit of priority under 35 U.S.C. § 119(e) from U.S. Provisional Patent Application Ser. No. 61/719,691, filed Oct. 29, 2013, the entirety of each of which is expressly incorporated herein by reference in its entirety.

GOVERNMENT SUPPORT

This invention was made with Government support under GM071461 awarded by the National Institutes of Health. The Government has certain rights in this invention.

BACKGROUND OF THE INVENTION

Compared to DNA, molecular recognition of double stranded RNA has received relatively little attention. Until the early 90's, RNA was viewed as a passive messenger in the transfer of genetic information from DNA to proteins. However, since the discovery that RNA can catalyze chemical reactions, the number and variety of non-coding RNAs and the important roles they play in biology have been growing steadily. [1] Currently, the functional importance of most RNA transcripts is still unknown and it is likely that many more regulatory RNAs will be discovered in the near future. The ability to selectively recognize and control the function of such RNAs will be highly useful for both fundamental research and practical applications. However, recognition of double helical RNA by sequence selective ligand binding is a formidable challenge. [2, 3]

Double-helical RNA has become an attractive target for molecular recognition because many noncoding RNAs play important roles in the control of gene expression. Recently, short peptide nucleic acids (PNA) were found to bind strongly and sequence selectively to a homopurine tract of double-helical RNA via formation of a triple helix.

Biologically relevant double helical RNAs may be recognized by major groove triple helix formation using peptide nucleic acid (PNA). [4-6] PNAs as short as hexamers form stable and sequence selective Hoogsteen triple helices with RNA duplexes ($K_a > 10^7$ M$^{-1}$) at pH 5.5. [4] A limitation of triple helical recognition was the requirement for long homopurine tracts, as only the Hoogsteen T(U)*A-T(U) and C+*GC triplets could be used (FIG. 1). Modification of PNA with 2-pyrimidinone [7] and 3-oxo-2,3-dihydropyridazine (E) [8] nucleobases allowed efficient and selective recognition of isolated C-G and U-A inversions, respectively, in polypurine tracts of double helical RNA at pH 6.25. [5, 6] However, the high affinity of PNA at pH 5.5 was greatly reduced at pH 6.25 and no binding could be observed at physiologically relevant salt and pH 7.4. [5] The remaining problem was the unfavorable protonation of cytosine, which was required for formation of the Hoogsteen C+*G-C triplets (FIG. 1). Because its pK$_a$=4.5, cytosine is hardly protonated under physiological pH, which greatly decreases the stability of the triple helix.

Povsic and Dervan pioneered the chemical modulation of the cytosine pKa by showing that triple helices containing 5-methylcytosine were more stable at higher pH than those of unmodified DNA. [10] More recently, derivatives of 2-aminopyridine have been used to increase the stability of DNA triple helices at high pH. [11-14]

An alternative approach has used neutral nucleobases that mimic the hydrogen-bonding scheme of protonated cytosine. The most notable examples are pseudoisocytosine (abbreviated as J in FIG. 1) by Kan and co-workers, [15] methyloxocytosine by McLaughlin and co-workers, [16, 17] and a pyrazine derivative by von Krosigk and Benner. [18] The J base is widely used in PNA to alleviate the pH dependency of PNA-DNA triplexes. [19, 20]

Practical applications of triple-helical recognition of nucleic acids are limited by (1) the low stability and slow formation of the triplex caused, at least in part, by electrostatic repulsion between the negatively charged phosphate backbones of the double helix and the incoming third-strand oligonucleotide and (2) the requirement for long homopurine tracts, as only U*A-U and C*G-C triplets are used in the common triple-helical recognition. However, it was recently shown that short peptide nucleic acids (PNA) recognize double-helical RNA via highly stable and sequence selective triple-helix formation. [10-12] PNA, as short as hexamers, formed triple helices with a RNA duplex faster and with higher affinity than with RNA as the third strand. Furthermore, nucleobase modifications allowed recognition of isolated pyrimidine inversions in short polypurine tracts, thus expanding the potential of recognition to biologically relevant double-helical RNA, such as rRNA and microRNAs. [12]

SUMMARY OF THE INVENTION

These findings inspired a hypothesis that, because of the absence of a negatively charged backbone, PNA will be a superior candidate for triple-helical recognition of RNA and may overcome the limitations of natural oligonucleotides in triple-helical recognition. Interestingly, despite extensive studies of DNA-PNA triplexes, binding of PNA to double-helical RNA had not been previously studied. The potential of chemically modified PNA in molecular recognition of double-helical RNA was therefore explored. The use of modified heterocycles to recognize double stranded RNA at physiologically relevant conditions also had not been studied.

The present invention provides an efficient solution to the binding problem and demonstrates that sequence selective recognition of the RNA duplex can be achieved at physiologically relevant conditions by replacing cytosine with a more basic (pK$_a$=6.7 [9]) heterocycle, 2-aminopyridine (abbreviated as M in FIG. 1).

It is an object to provide a peptide nucleic acid (PNA), comprising 2-aminopyridine nucleobases replacing cytosines in a PNA sequence, configured to form stable and sequence selective triple helices with double stranded RNA at physiological conditions, e.g., pH 7.4 and/or 37° C.

It is also an object to provide a method of forming a PNA-dsRNA triple helix which is stable at physiological conditions, e.g., pH 7.4 and/or 37° C., comprising replacing at least one cytosine of the PNA with a 2-aminopyrimidine nucleobase.

Other objects will become apparent from a review of the description herein.

DESCRIPTION OF THE PREFERRED EMBODIMENTS

Example 1

Figure 1:
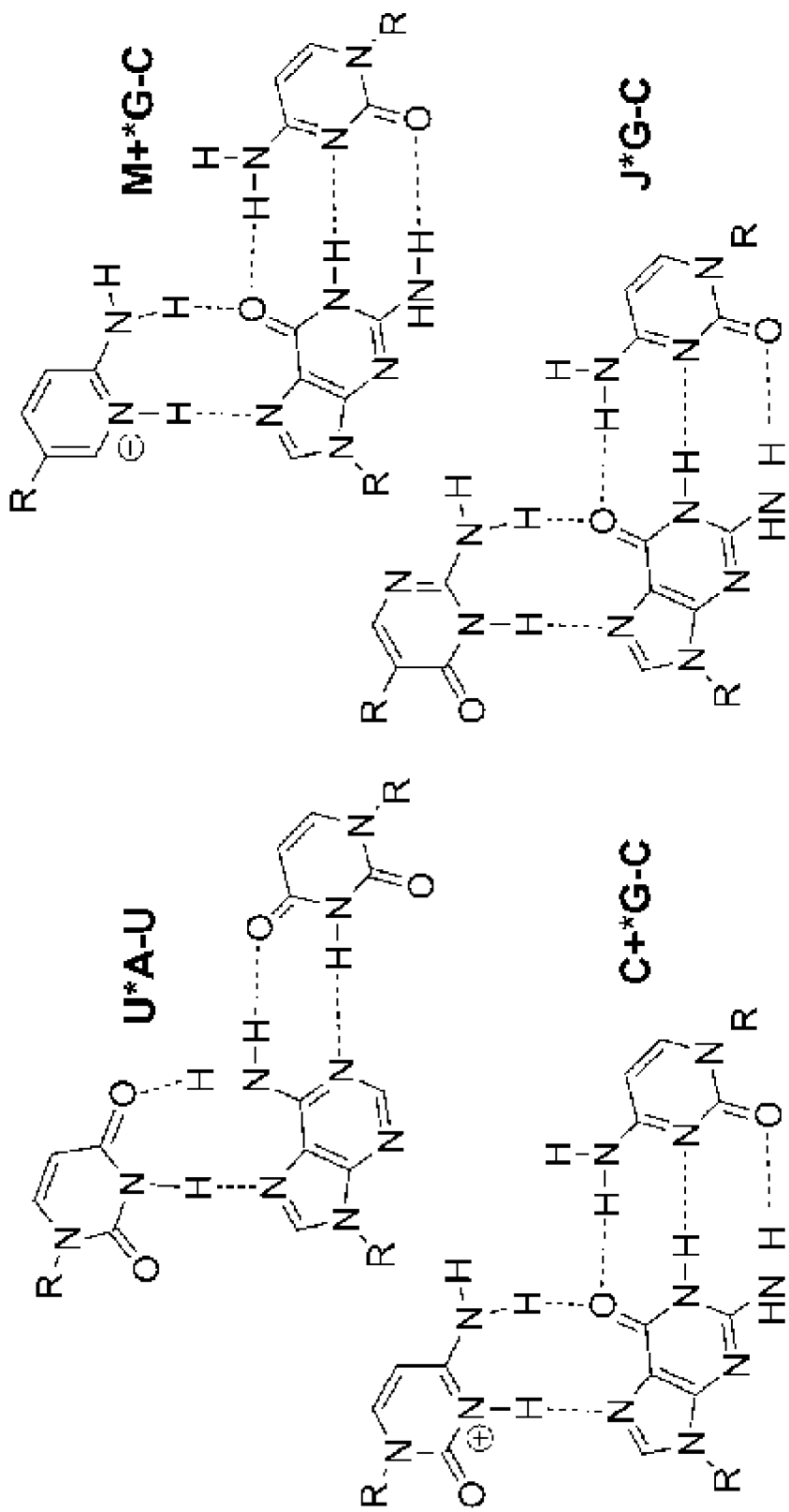
FIG. 1 shows standard and modified Hoogsteen triplets.
Figure 2:
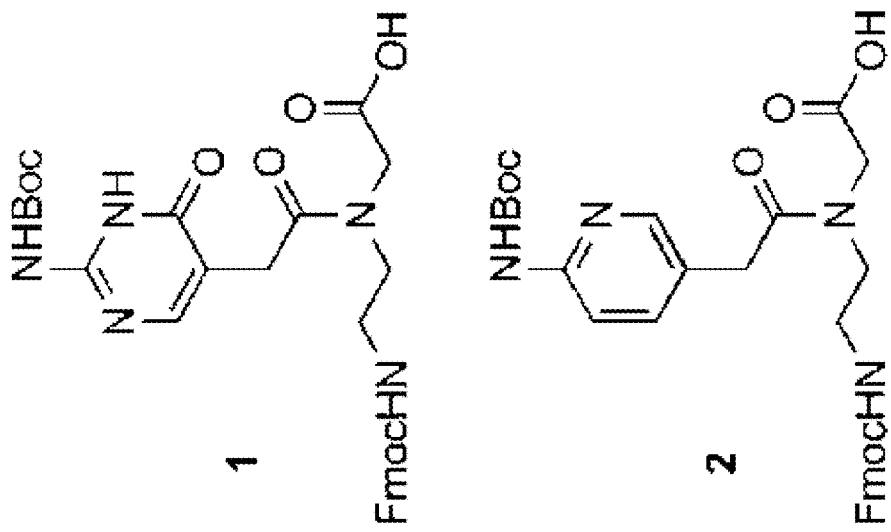
FIG. 2 shows RNA, PNA, and DNA sequences used to compare C, J, and M nucleobases.
Figure 2:
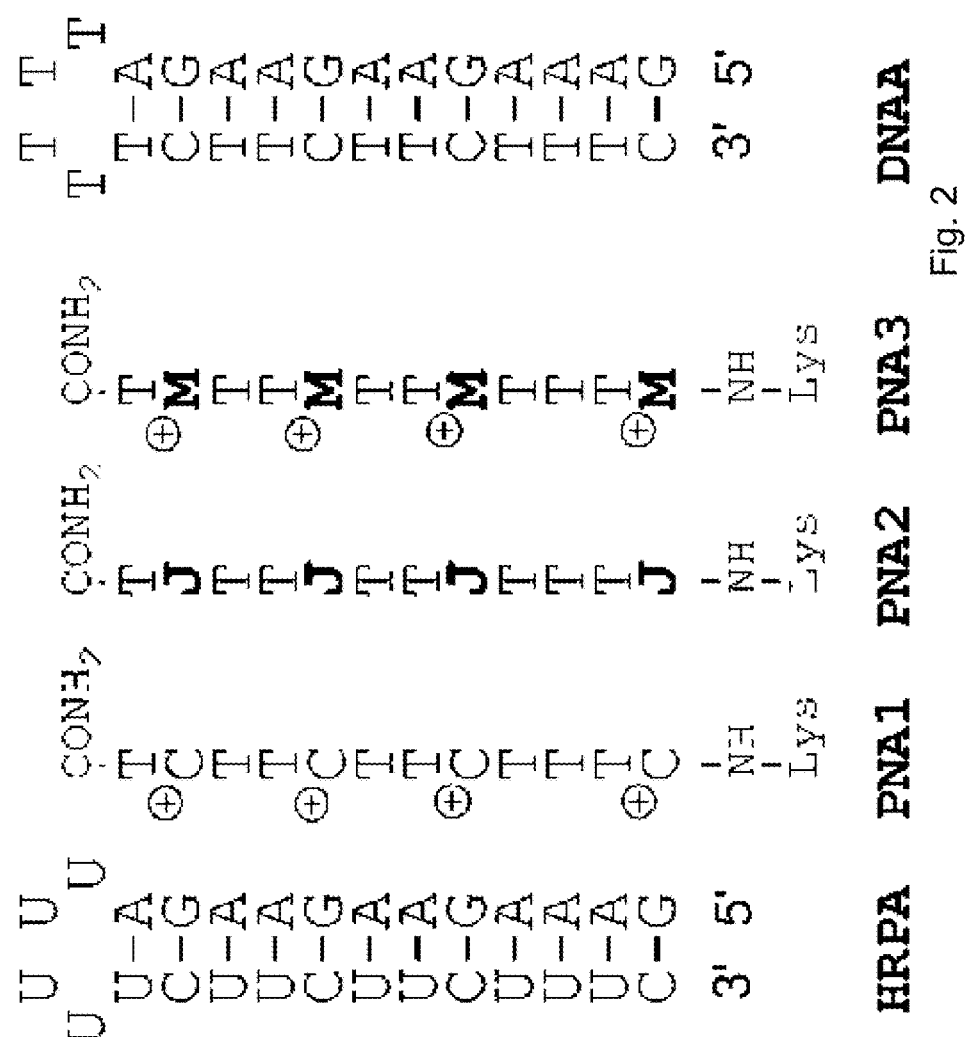

FIG. 2 compares the binding of unmodified PNA1, J modified PNA2 and M-modified PNA3 to HRPA, an Arich RNA hairpin similar to the model systems used previously. [4, 5] Fmoc-protected J monomer 1 was synthesized according to the literature procedure. [21] The M monomer 2 was synthesized from Fmoc-protected PNA backbone 3 and the known carboxylic acid 4 using DCC mediated coupling followed by deprotection of the allyl group as previously described (Scheme 1). [5] All PNAs were synthesized using a standard PNA protocol on an Expedite 8909 DNA synthesizer, purified by HPLC and characterized by mass spectroscopy as previously reported. [4-6]

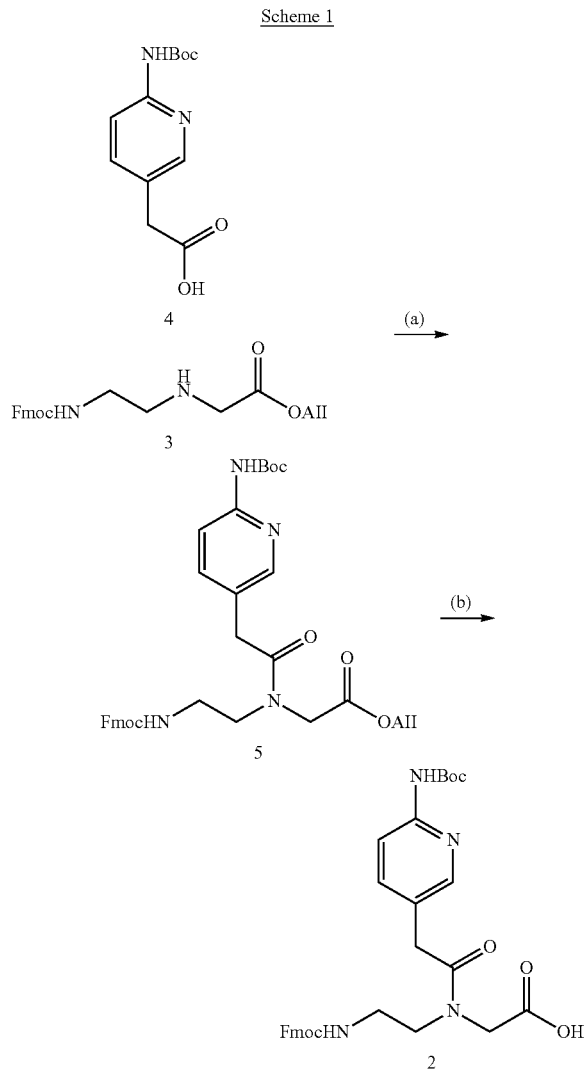

Scheme 1

Synthesis of M PNA monomer: a) DCC, 3-hydroxy-1,2,3-benzotriazin-4(3H)-one, DMF, RT, overnight, 57%; b) [Pd(PPh3)4], N-ethylaniline, THF, RT, 2 h, 79%.

Following the same approach as in our previous studies, [4-6] isothermal titration calorimetry (ITC) and UV thermal melting were used to characterize the binding of PNA to RNA hairpins. ITC directly measures the enthalpy of binding and, through fitting of the binding data, provides binding affinity (association constant $K_a$ in $M^{-1}$) and stoichiometry (the ratio of PNA to RNA in the final complex). [22] Due to operational simplicity, reliability and rich thermodynamic data, ITC is one of the best methods to study ligand binding to RNA. The unmodified PNA1 formed a stable triplex with HRPA at pH 5.5 (Table 1) in sodium acetate buffer at 25° C.

TABLE 1

| Binding of C, J and M containing PNA to RNA HRPA. [a] | | | |
|---|---|---|---|
| PNA | Acetate pH 5.5 [b] | Acetate pH 7.0 [b] | Phosphate pH 7.4 [c] |
| PNA1 (C) | 0.76 | 0.06 | NB |
| PNA2 (J) | — | 0.41 | 0.17 |
| PNA3 (M) | — | 36.5 | 1.8 |

[a] Association constants $K_a \times 10^7$ $M^{-1}$, NB—no binding, $K_a < 10^3$
[b] 100 mM sodium acetate buffer, pH 5.5 at 25° C.
[c] 2 mM $MgCl_2$, 90 mM KCl, 10 mM NaCl, 50 mM potassium phosphate at 37° C.

As expected, because of the unfavorable protonation of cytosine at higher pH, the affinity decreased significantly when the pH of the buffer was increased to 7 and no binding in phosphate buffer mimicking the physiological conditions at 37° C. was observed.

The affinity of PNA1 at pH 5.5 was used as a benchmark to gauge the effect of J and M modifications on PNA affinity at higher pH. The affinity of J-modified PNA2 for HRPA in acetate buffer at pH 7 was lower than the affinity of PNA1 at pH 5.5 and decreased even more under the more demanding physiological conditions (Table 1). Nielsen and co-workers [20] reported that the affinity of an unmodified PNA 15 mer (having 5 isolated cytosines) for a DNA duplex dropped by three orders of magnitude (Kd changed from 2 nM to 2.2 mM) when changing the pH from 5.5 to 7.2. Substitution of all five cytosines by J base increased the affinity only about tenfold (Kd=0.15 mM). [20] Thus, the result in Table 1 was qualitatively consistent with that reported by Nielsen, only smaller in magnitude, and suggested that the positive charge on cytosine contributed significantly to stability of the Hoogsteen triplet, presumably via electrostatic attraction to the negatively charged nucleic acid. Consequently, an ideal design for recognition of G-C pairs would include both a correct hydrogen bonding scheme and a positive charge on the heterocycle. Because unmodified PNA containing cytosine (pKa=4.5) forms a stable triple helix at pH 5.5, PNA modified with 2-aminopyridine M (pKa=6.7) was hypothesized to form at least equally strong triple helices at physiological pH 7.4 (due to a similar pH/pKa difference).

Confirming this hypothesis isothermal titration calorimetry (ITC) showed that M modification strongly enhanced the binding affinity of PNA3. In acetate buffer at pH 7 M-modified PNA3 had about two orders of magnitude higher affinity (Ka=$3.7 \times 10^8$) for HRPA than the J-modified PNA2 (FIG. 2 and Table 1). Under physiologically relevant conditions PNA3 bound to HRPA with Ka=$1.8 \times 10^7$, which was an order of magnitude higher than the affinity of PNA2 at the same conditions and twice that of unmodified PNA1 at pH 5.5. The larger drop in affinity for PNA3 compared to PNA2 going from acetate to phosphate buffer is most likely due to screening of the electrostatic interactions (that are more important for the charged M) by higher salt concentration and the presence of $MgCl_2$ in the physiologically relevant buffer. Most remarkably, binding of PNA3 to the matched DNA hairpin (DNAA) in physiological phosphate buffer was about two orders of magnitude weaker (Ka=3× $10^5$) than binding to RNA HRPA. This result suggested that the M-modified PNA might have unique selectivity for triple helical recognition of RNA over DNA. For all experiments at physiologically relevant conditions, fitting of ITC titration curves gave a 1:1 PNA:RNA stoichiometry (see Table 2) consistent with the triple helix formation.

TABLE 2

Experimental ITC data.

| | Sequence | Ka | ΔH | ΔS | ΔG | Stoichiom. |
|---|---|---|---|---|---|---|
| HRPA | PNA1 (5.5) | 7.58E+06 | −55.7 | −155 | −9.4 | 1.2 |
| | PNA1 (7.0) | 5.65E+05 | −105.1 | −326 | −7.8 | 0.5 |
| | PNA2 (7.0) | 4.10E+06 | −27.9 | −63 | −9.0 | 1.3 |
| | PNA2 (7.4) | 2.20E+06 | −17.9 | −31 | −8.6 | 1.1 |
| | | 1.10E+06 | −14.8 | −22 | −8.2 | 1.1 |
| | average | 1.65E+06 | −16.4 | −27 | −8.4 | 1.1 |
| | standard dev | 7.78E+05 | 2.2 | 6 | 0.3 | 0.0 |
| | PNA3 (7.0) | 4.20E+08 | −64.5 | −177 | −11.8 | 0.9 |
| | | 3.10E+08 | −67.4 | −187 | −11.6 | 0.8 |
| | average | 3.65E+08 | −65.9 | −182 | −11.7 | 0.9 |
| | standard dev | 7.78E+07 | 2.0 | 7 | 0.1 | 0.1 |
| | PNA3 (7.4) | 1.40E+07 | −76.4 | −224 | −9.7 | 0.8 |
| | | 2.10E+07 | −80.3 | −236 | −10.0 | 0.7 |
| | average | 1.75E+07 | −78.3 | −230 | −9.9 | 0.8 |
| | standard dev | 4.95E+06 | 2.7 | 8 | 0.2 | 0.1 |
| DNAA | PNA3 (7.4) | 2.00E+05 | −5.3 | 7 | −7.2 | 1.0 |
| | | 3.70E+05 | −46.8 | −132 | −7.6 | 0.9 |
| | average | 2.85E+05 | −26.0 | −62 | −7.4 | 1.0 |
| | standard dev | 1.20E+05 | 29.4 | 98 | 0.3 | 0.1 |
| HRP1 | PNA5 (7.4) | 1.10E+07 | −46.1 | −122 | −9.6 | 1.0 |
| | | 2.80E+07 | −38.0 | −93 | −10.2 | 1.2 |
| | average | 1.95E+07 | −42.0 | −108 | −9.9 | 1.1 |
| | standard dev | 1.20E+07 | 5.7 | 21 | 0.4 | 0.1 |
| HRP2 | PNA6 (7.4) | 4.18E+06 | −37.7 | −96 | −9.0 | 1.1 |
| | PNA6A (7.4) | 5.00E+05 | −19.6 | −40 | −7.8 | 1.0 |
| HRP7 | PNA7 (7.4) | 1.38E+07 | −103.9 | −316 | −9.7 | 0.7 |
| | | 1.05E+07 | −85.5 | −255 | −9.6 | 1.0 |
| | average | 1.22E+07 | −94.7 | −285 | −9.7 | 0.9 |
| | standard dev | 2.33E+06 | 13.0 | 43 | 0.1 | 0.2 |

UV thermal melting experiments confirmed the ITC results. Consistent with previous observations, [4] the complexes of HRPA and high affinity PNAs melted in one transition of triple helix to single strands without an intermediate duplex. In phosphate buffer at pH 7.4 adding PNA2 had little effect on the stability of HRPA: $t_m$=75° C. for HPRA alone and 74° C. for a 1:1 complex of HRPA-PNA2. Consistent with the higher Ka observed in the ITC experiments, the thermal stability of a 1:1 complex of HRPA-PNA3 was significantly higher at 80° C. Taken together, the results confirmed the hypothesis that the charged M would have an advantage over the neutral J for triple helical recognition of RNA.

Figure 3:
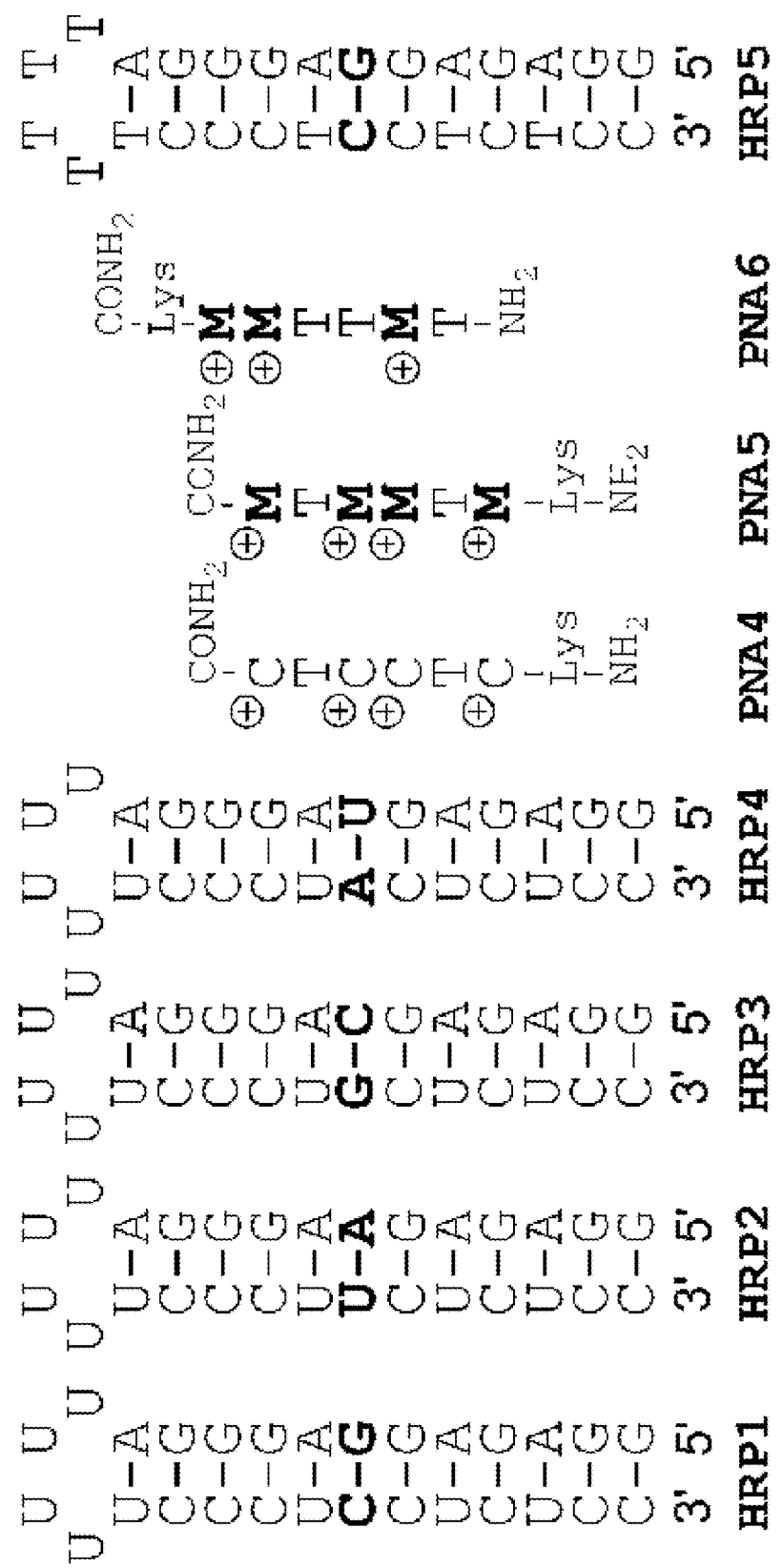
FIG. 3 shows PNA, RNA, and DNA used in the sequence specificity study.

Next the sequence specificity of M-modified PNA was probed using a model system from previous studies (FIG. 3). [4, 5] Table 3 shows that PNA5 (four M modifications) had high affinity for the matched HRP1 at physiologically relevant conditions while maintaining excellent sequence specificity. The binding affinity of M-modified PNA5 at pH 7.4 was somewhat lower than that of unmodified PNA4 at pH 5.5. [4] This was in contrast to a similar comparison of M-modified PNA3 and unmodified PNA1 in Table 1. The discrepancy might be related to electrostatic repulsion of adjacent charged nucleobases, which has been reported to have a negative effect on affinity, [23] and may affect PNA5 more than PNA4. Nevertheless, the strong and highly selective RNA binding by PNA5 at physiologically relevant conditions was extremely encouraging. UV thermal melting of the matched PNA5-HRP1 complex showed a broad and relatively weak transition at ~55° C. that might be assigned to triplex melting preceding the melting of the HRP1 hairpin at ~100° C. Similar transitions unique to the matched PNA5-HRP1 complex were also observed in CD melting plots. Consistent with the high sequence selectivity, no transitions above 30° C. were observed that could be assigned to triplex melting of the mismatched complexes. Confirming the unique RNA selectivity observed for PNA3, PNA5 showed little, if any binding to its matched DNA hairpin HRP5.

TABLE 3

Binding of M-modified PNA to RNA Harpins [a]

| PNA | HRP1 (G-C) | HRP2 (A-U) | HRP3 (C-G) | HRP4 (U-A) |
|---|---|---|---|---|
| PNA4 [b] | 8.4 | 0.04 | 0.05 | 0.02 |
| PNA5 [c] | 2.0 | <0.001[d] | NB[e] | NB[e] |
| PNA6 [c] | NB [e] | 0.4 | NB[e] | NB[e] |

[a] Association constants $K_a \times 10^7 M^{-1}$
[b] From ref. 4, in 100 mM sodium acetate buffer, pH 5.5 at 25° C.
[c] In Phosphate buffer, pH 7.4 at 37° C.
[d] Highest estimate, the low binding prevented more accurate curve fit
[e] NB—no binding, $K_a<10^3$.

PNA6 (three M modifications) had five times lower affinity for the matched HRP2 than PNA5 for HRP1, which was consistent with a higher stability of triplets involving G-C base pairs and the notion that the positive charges are important for high binding affinity. As expected, PNA6 showed excellent sequence specificity. The PNA-RNA stoichiometry was 1:1 in all experiments shown in Table 3 (see Table 2).

Figure 4:
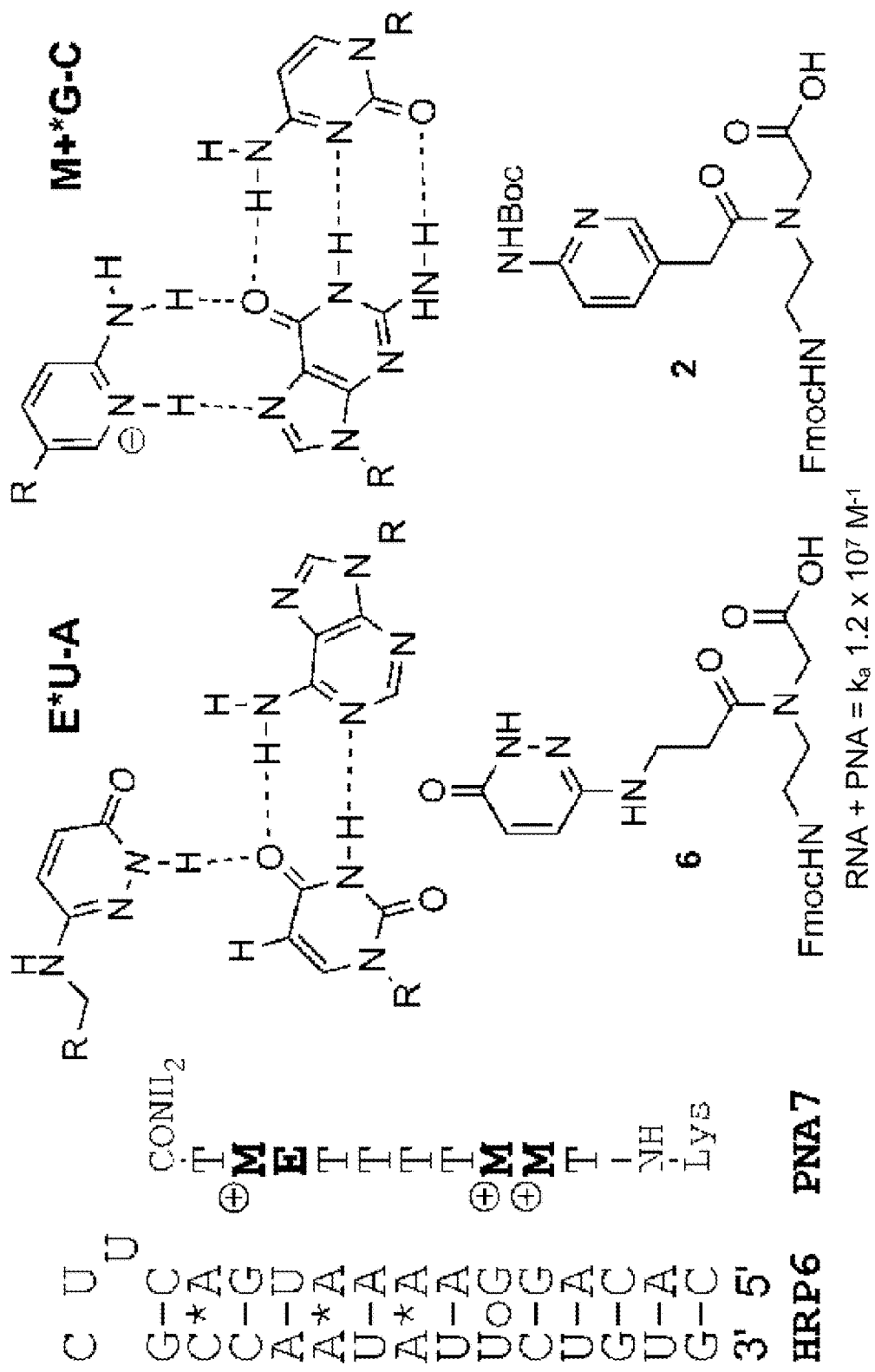
FIG. 4 shows binding of E- and M-modified PNA7 to HRP6 to model the pri-miRNA-215 hairpin structure.

Finally, microRNA-215, which is implicated in cancer development and drug resistance, [24, 25] was selected as an initial target to check if M-modified PNA could bind to biologically relevant double helical RNA. MicroRNAs (miRNAs) are transcribed as long hairpin structures, pri-miRNAs, which are processed into mature miRNA duplexes (~22 nt) by Drosha and Dicer endonucleases. It is common to find stretches of eight and more contiguous purines interrupted by one or two pyrimidines in pri-miRNA hairpins. [26] Triple helical binding to such sites could be used to detect miRNAs and interfere with their function, which would find broad applications in fundamental science, medicine and biotechnology. HRP6 was chosen as a model that contains the purine rich recognition site present in pri-miRNA-215. [26] HRP6 has a stretch of nine purines interrupted by a uridine and features several non-canonical base pairs, which are hallmarks of pri-miRNA hairpins. For recognition of the uridine interruption nucleobase E (FIG. 4) that was originally designed for thymidine recognition in DNA [8] and later adopted for uridine recognition in RNA was used. [5] PNA7 having three M and one E modification was prepared using monomers 2 and the previously reported [5] 6 (FIG. 4).

Consistent with results obtained with other M-modified PNAs, PNA7 recognized HRP6 with high affinity (Ka=1.2× $10^7$) and 1:1 stoichiometry (Table 2) under physiologically relevant conditions. Remarkably, the non-canonical C*A and A*A and the wobble UoG base pairs did not prevent formation of the PNA-RNA complex.

In summary, modification of PNA with 2-aminopyridine (M) nucleobases has been demonstrated to allow formation of stable and sequence selective triple helices with double stranded RNA at physiologically relevant conditions. For triple helical RNA recognition, modulation of nucleobase basicity (c.f., pKa=6.7 for M with 4.5 for C) was a more efficient approach than using the neutral J base. The M-modified PNAs exhibited unique RNA selectivity and had two orders of magnitude higher affinity for the double stranded RNAs than for the same DNA sequences. It is conceivable that the deep and narrow major groove of RNA presented a better steric fit for the PNA ligands than the wider major groove of DNA. In preliminary experiments nucleobase-modified PNA recognized a purine rich model sequence of a double helical miRNA precursor with high affinity at physiologically relevant conditions. While this is a relatively new area of research, Beal and co-workers [27] have already demonstrated the potential of targeting pri-miRNAs using helix-threading peptides. Taken together the present results suggest that PNA may have unique and previously underappreciated potential for triple helical recognition of biologically relevant RNA. Low stability at pH 7.4 has been a long-standing problem for practical applications of triple helices. The excellent performance of M modified PNAs at pH 7.4 observed herein provide efficient solution to this problem that should open the door for new approaches to detection and interference with the function of double stranded RNA molecules.

Synthesis of (6-tert-butoxycarbonylaminopyridin-3-yl) acetic Acid (4)

Ethyl (6-tert-butoxycarbonylaminopyridin-3-yl)acetate [Burns, C. J.; Goswami, R.; Jackson, R. W.; Lessen, T.; Li, W.; Pevear, D.; Tirunahari, P. K.; Xu, H. Beta-lactamase inhibitors. W2010/130708 PCT/EP2010/056408: patent, 2010; pp 197.] (4.4 g, 15.7 mmol) and NaOH (1.3 g, 32.5 mmol) were dissolved in of methanol/water (1:1, 30 mL) and refluxed for 1.5 hours. The solution was cooled and the product was precipitated by adding 20% aqueous citric acid. The precipitate was filtered, washed with dichloromethane/hexanes (1:1, 20 mL) and dried to give 1.4 g of 4 (49%) as pale yellow solid.). $^1$H NMR (DMSO-d6, 600 MHz) δ: 12.54 (s, 1H), 9.72 (s, 1H), 8.12 (s, 1H), 7.75-7.73 (d, 1H), 7.63-7.62 (d, 1H), 3.55 (s, 2H), 1.48 (s, 9H). $^{13}$C NMR (DMSO-d6, 90.5 MHz) δ: 172.4, 152.7, 151.1, 148.1, 138.8, 125.1, 111.9, 79.5, 337.0, 28.1.

Synthesis of allyl 2-(N-(2-(Fmoc)ethyl)-2-(6-(tert-butoxycarbonylamino)pyridin-3-yl)acetamido)acetate (5)

(6-tert-butoxycarbonylaminopyridin-3-yl) acetic acid 4 (0.20 g 0.79 mmol), PNA backbone 3 [Wojciechowski, F.; Hudson, R. H. E. *J. Org. Chem.* 2008, 73, 3807.] (0.27 g, 0.72 mmol) and 3-hydroxy-1,2,3-benzotriazin-4(3H)-one (0.13 g, 0.80 mmol) were dissolved in anhydrous dimethylformamide (5 mL). The solution was cooled on ice and N,N'-dicyclohexylcarbodiimide (0.18 g, 0.88 mmol) was added. After 1 hour, the ice bath was removed and the solution was left to stir overnight at room temperature. The reaction mixture was evaporated, dissolved in dichloromethane (16 mL) and washed with 5% aqueous NaHCO3 (2×20 mL). The organic layer was dried over Na2SO4 and evaporated under reduced pressure. The product was purified by silica gel column chromatography using 20-80% of ethyl acetate in hexane to give 0.25 g of 6 (57%). Rf=0.35 (5% v/v of methanol in dichloromethane). $^1$H NMR (DMSO-d6, 600 MHz) δ: 8.02-8.00 (d, 1H), 7.83-7.800 (t, 1H), 7.69-7.67 (d, 2H), 7.56 (s, 1H), 7.51-7.50 (d, 2H), 7.48 (s, 1H), 7.33-31 (d, 2H), 7.24-7.23 (t, 2H), 5.87-5.80 (m, 1H), 5.65-6.34 (t, 1H), 5.29-5.26 (d, 1H), 5.23-5.21 (d, 1H), 5.20-5.18 (d, 1H), 4.59-58 (d, 1H), 4.56-4.55 (d, 1H), 4.36-4.35 (d, 1H), 4.29-4.28 (d, 2H), 4.14-4.12 (t, 1H), 4.04 (s, 1H), 3.96 (s, 2H), 3.55 (s, 2H), 3.51-3.49 (t, 2H), 3.45 (s, 2H), 3.31-3.30 (d, 2H), 3.28-3.28 (d, 2H), 1.43 (s, 9H). $^{13}$C NMR (DMSO-d6, 90.5 MHz) δ: 171.7 (171.3), 169.9, 169.0, 156.6, 152.3, 151.0, 147.8, 143.8, 143.8, 141.3, 139.0, 131.4, 131.1, 127.8, 127.1, 125.1, 125.0, 124.7, 120.0, 120.0, 119.8, 119.1, 112.1, 81.0, 66.9 (66.6), 66.2, 49.6, (49.2), 47.2, 39.5, 37.0, 36.3, 28.3.

Synthesis of 2-(N-(2-(Fmoc)ethyl)-2-(6-(tert-butoxycarbonylamino)pyridin-3-yl)acetamido) acetic Acid (2)

2-(N-(2-(Fmoc)ethyl)-2-(6-(tert-butoxycarbonylamino) pyridin-3-yl)acetamido) acetate 5 (0.32 g, 0.52 mmol) was dissolved in anhydrous THF (12 mL). Pd(PPh3)4 (0.025 g, 0.022 mmol) and N-ethylaniline (120 μl, 0.96 mmol) were added and the reaction was stirred for 2 hours. The solvent was evaporated and the yellow residue was dissolved in ethyl acetate (25 ml, gentle warming may be required) and washed with saturated aqueous KHSO4 (3×20 mL), water (3×20 mL) and brine (3×20 mL). The organic layer was dried over Na2SO4 and evaporated under reduced pressure. The product was purified by silica gel column chromatography using ethyl acetate to give 0.24 g of 2 (79%). For best results, compound 2 should be used in PNA synthesis immediately after preparation. $^1$H NMR (DMSO-d6, 360 MHz) δ: 9.95 (s, 1H), 8.02 (d, 1H), 7.72 (s, 1H), 7.65-7.63 (t, 2H), 7.52-7.50 (d, 2H), 7.47-7.45 (d, 1H), 7.23-7.19 (t, 2H), 5.60 (s, 1H), 4.45 (d, 2H), 4.37-4.36 (d, 1H), 4.29-4.27 (d, 1H), 4.12-4.10 (t, 2H), 3.94 (s, 2H), 3.59 (s, 2H), 3.56 (s, 1H), 3.48 (s, 1H) 3.39 (s, 1H), 3.32-3.31 (d, 2H), 3.24 (s, 1H), 1.40 (s, 9H). $^{13}$CNMR (DMSO-d6, 90.5 MHz) δ: 171.0, 156.2, 152.7, 150.6, 148.2, 140.7, 139.5, 138.9, 128.9, 127.5, 127.3, 127.1, 126.5, 125.3, 125.1, 120.1 (120.0), 111.8 (111.8), 79.4 (79.4), 65.6, 46.8, 38.3, 35.8, 28.2 (28.1). HRMS ESI-TOF found m/z 575.2507 [M+H]+, calculated for $C_{31}H_{34}N_4O_7$: 574.2427.

RNA was purchased from Dharmacon Inc. and deprotected according to manufacturer's recommendations. After deprotection RNA samples were purified using RP-HPLC on Xbridge Prep C-18 column (5 μm, 10 mm×150 mm) at 60° C. eluting with a linear gradient (5%-20%) of mobile phase B in mobile phase A over 40 min, flow rate 5 ml/min. Mobile phase A was 0.1 M of triethylammonium acetate (pH=7.0) in HPLC water and mobile phase B was a mixture of 0.1 M of triethylammonium acetate (pH=7.0) in HPLC water and HPLC grade acetonitrile (60/40, v/v). Absorbency was monitored at a wavelength of 254 nm and 280 nm, and the fraction containing the major peak was collected, lyophilized to dryness to afford pure RNA samples. RNA was quantified using the extinction coefficient provided by Dharmacon.

ITC Experiments were done on a Nano ITC G2 (TA Instruments). RNA stock solution (17.5 μL, 0.24 mM) was evaporated to dryness and the solid was dissolved in 1.6 mL of phosphate buffer (2 mM MgCl2, 90 mM KCl, 10 mM NaCl, 50 mM potassium phosphate at pH 7.4). After degassing, the RNA solution (0.95 mL, 0.002625 mM) was loaded into ITC reaction cell and the reference cell was loaded with degassed HPLC water. PNA stock solution (70 μL, 0.24 mM) was evaporated to dryness and the solid was dissolved in 350 µL of acetate buffer. After degassing the PNA solution (250 µL, 0.048 mM) was loaded in titration syringe. The syringe was inserted into reaction cell and the instrument was equilibrated at 37° C. until the baseline was flat and stable. The following parameters were used:

Experiment type: Incremental titration
Stirring rate=250 rpm
Temperature set point=37° C.
Syringe size=250 µl
Equilibration time=300 sec
Interval of individual injection=260-800 sec
Number of injections=50
Volume of individual injection=5 µl The titration data were analyzed using NanoAnalyze software (TA Instruments) and independent model to obtain the fitting graph and thermodynamic data of the experiments.

UV melting of each RNA (5.25 µM) and PNA (5.25 µM) complexes was done in phosphate buffer (2 mM $MgCl_2$, 90 mM KCl, 10 mM NaCl, 50 mM potassium phosphate at pH 7.4). Absorbance vs. temperature profiles were measured at 260 nm on Shimadzu 800 UV-visible spectrometers equipped with a six or eight position Peltier temperature controllers, respectively. The temperature was increased at a rate of 0.5° C. per minute. The melting temperatures were obtained using Shimadzu LabSolutions Tm Analysis (Version 1.2.1.0) software. The experimental absorbance vs. temperature curves were converted into a fraction of strands remaining hybridized (a) vs. temperature curves by fitting the melting profile to a two-state transition model, with linearly sloping lower and upper base lines. The melting temperatures (c) were obtained directly from the temperature at $\alpha=0.5$.

Synthesis of PNA was done on Expedite 8909 synthesizer following the standard manufacturers protocol (2 µmol scale) and using NovaSyn TG Sieber resin (Novabiochem) as a support, HATU as an activator and Fmoc-PNA-A(Bhoc)-OH, Fmoc-PNA-C(Bhoc)-OH, Fmoc-PNA-G(Bhoc)-OH and Fmoc-PNA-T-OH as monomers (purchased from Link Technologies Ltd, UK). L-lysine was coupled to N-terminus of PNA on Expedite 8909 (using standard PNA coupling protocol) using Fmoc-L-lys(Boc)-OH and HATU. Chain extension followed a three-step cycle: (i) removal of the Fmoc-protecting group from the terminal amine with 20% piperidine in DMF, (ii) coupling of the next monomer onto the N-terminus of the growing chain with HATU, and (iii) capping of the unreacted amines with acetic anhydride. Treating the solid resin with m-cresol/TFA (2:8) mixture for 2 h resulted in simultaneous removal of the protecting groups and cleavage of the oligomers from the resin. The crude PNA samples were precipitated from anhydrous ether. The solid was collected, dried, dissolved in HPLC grade water and purified by RP-HPLC on Xbridge Prep C-18 column (5 µm, 10 mm×150 mm) at 60° C. eluting with a linear gradient of acetonitrile in water containing 0.1% of TFA over 40 min. Absorbency was monitored at 254 nm and 280 nm, and the fraction containing the major peak was collected, lyophilized to dryness to afford pure PNA samples. The PNA was quantified following procedure described for DNA and RNA. [Puglisi, J. D.; Tinoco, I., Jr., Absorbance melting curves of RNA. *Methods Enzymol.* 1989, 180, 304-325.] The molecular weight of the synthesized PNAs was confirmed by ESI mass spectrometry:

PNA1. ESI found m/z 3278.7 $[M+H]^+$, calculated for $C_{134}H_{180}N_{55}O_{45}$: 3279.3.

PNA2. ESI found m/z 3279.7 $[M+H]^+$, m/z 1094.5 $[M+3H]^{3+}$, m/z 821.1 $[M+4H]^{4+}$, calculated for $C_{134}H_{180}N_{55}O_{45}$: 3279.3.

PNA3. ESI found m/z 1607.2 $[M+2H]^{2+}$, m/z 1071.4 $[M+3H]^{3+}$, m/z 803.8 $[M+4H]^{4+}$, calculated for $C_{138}H_{183}N_{51}O_{41}$ 3212.3.

PNA5. ESI found m/z 1616.4 $[M+H]^+$, calculated for $C_{72}H_{100}N_{27}O_{17}$: 1615.7.

PNA6. ESI found m/z 1646.6 $[M+H]^+$, calculated for $C_{72}H_{100}N_{27}O_{19}$: 1647.7.

PNA7. ESI found m/z 2710.6 $[M+H]^+$, calculated for $C_{116}H_{156}N_{44}O_{34}$: 2711.8.

Binding of PNA to A-site RNA had not been previously studied. [12] The results show that unmodified PNA were able to bind the polypurine tract of bacterial A-site RNA in preference to human A-site RNA. The relatively low affinity and modest sequence selectivity of binding were most likely due to the inability of Hoogsteen triplets to recognize the pyrimidine interruption in the polypurine tract of HRP6. The results with PNA11 and PNA2 are encouraging for triplex recognition of A-site RNA, providing that a modified heterocycle could be designed that would recognize the pyrimidine interruption in the polypurine tract and restore binding affinity and sequence selectivity. [88-90] Consistent with this notion, incorporation of modified heterocyles [P and Pex (FIG. 11)], recently developed by us to recognize cytosine in G-C inversion, [62] significantly increased the sequence selectivity while maintaining excellent affinity in the triple-helical binding mode (Table 6). A brief review of secondary structure databases of noncoding RNAs reveals that it is relatively common to find short homopurine tracts of eight and more contiguous purines, sometimes interrupted by one or two pyrimidines, in bacterial rRNAs (www.rna.ccbb.utexas.edu/) and micro RNAs (www.mirbase.org/). Preliminary results with PNA13 and PNA14 suggest the possibility of designing relatively small PNA analogues to recognize such binding sites. It is conceivable that further development of chemical modifications may allow general recognition of isolated pyrimidines in the context of the homopurine triple helix at physiological pH, which may open a novel way to recognize and interfere with function of noncoding RNAs.

REFERENCES

Each of the following is expressly incorporated by reference herein in its entirety:

[1] P. A. Sharp, *Cell* 2009, 136, 577-580.
[2] J. R. Thomas, P. J. Hergenrother, *Chem. Rev.* 2008, 108, 1171-1224.
[3] L. Guan, M. D. Disney, *ACS Chem. Biol.* 2012, 7, 73-86.
[4] M. Li, T. Zengeya, E. Rozners, *J. Am. Chem. Soc.* 2010, 132, 8676-8681.
[5] P. Gupta, T. Zengeya, E. Rozners, *Chem. Commun.* 2011, 47, 11125-11127.
[6] Pankaj Gupta, Oluwatoyosi Muse, and Eriks Rozners, "Recognition of Double-Stranded RNA by Guanidine-Modified Peptide Nucleic Acids", Biochemistry (2012), 51(1), 63-73.
[7] S. Buchini, C. J. Leumann, *Angew. Chem.* 2004, 116, 4015-4018; S. Buchini, C. J. Leumann, *Angew. Chem., Int. Ed.* 2004, 43, 3925-1224.
[8] A. B. Eldrup, O. Dahl, P. E. Nielsen, *J. Am. Chem. Soc.* 1997, 119, 11116-11117.
[9] L R. Stewart, M. G. Harris, *J. Org. Chem.* 1978, 43, 3123-3126.
[10] T. J. Povsic, P. B. Dervan, *J. Am. Chem. Soc.* 1989, 111, 3059-3061.

[11] S. Hildbrand, A. Blaser, S. P. Parel, C. J. Leumann, *J. Am. Chem. Soc.* 1997, 119, 5499-5511.

[12] S. A. Cassidy, P. Slickers, J. O. Trent, D. C. Capaldi, P. D. Roselt, C. B. Reese, S. Neidle, K. R. Fox, *Nucleic Acids Res.* 1997, 25, 4891-4898.

[13] D. A. Rusling, V. E. C. Powers, R. T. Ranasinghe, Y. Wang, S. D. Osborne, T. Brown, K. R. Fox, *Nucleic Acids Res.* 2005, 33, 3025-3032.

[14] D. L. Chen, L. W. McLaughlin, *J. Org. Chem.* 2000, 65, 7468-7474.

[15] A. Ono, P. O. P. Ts'o, L. S. Kan, *J. Am. Chem. Soc.* 1991, 113, 4032-4033.

[16] G. Xiang, W. Soussou, L. W. McLaughlin, *J. Am. Chem. Soc.* 1994, 116, 11155-11156.

[17] G. Xiang, R. Bogacki, L. W. McLaughlin, *Nucleic Acids Res.* 1996, 24, 1963-1970.

[18] U. von Krosigk, S. A. Benner, *J. Am. Chem. Soc.* 1995, 117, 5361-5362.

[19] M. Egholm, L. Christensen, K. L. Dueholm, O. Buchardt, J. Coull, P. E. Nielsen, *Nucleic Acids Res.* 1995, 23, 217-222.

[20] M. E. Hansen, T. Bentin, P. E. Nielsen, *Nucleic Acids Res.* 2009, 37, 4498-4507.

[21] R. H. E. Hudson, F. Wojciechowski, *Can. J. Chem.* 2008, 86, 1026-1029.

[22] A. L. Feig, *Methods Enzymol.* 2009, 468, 409-422.

[23] E. S. Priestley, P. B. Dervan, *J. Am. Chem. Soc.* 1995, 117, 4761-4765.

[24] B. Song, Y. Wang, M. A. Titmus, G. Botchkina, A. Formentini, M. Kornmann, J. Ju, *Molecular Cancer* 2010, 9, #96 pp. 1-10.

[25] Z. Jin, F. M. Selaru, Y. Cheng, T. Kan, R. Agarwal, Y. Mori, A. V. Olaru, J. Yang, S. David, J. P. Hamilton, J. M. Abraham, J. Harmon, M. Duncan, E. A. Montgomery, S. J. Meltzer, *Oncogene* 2011, 30, 1577-1585.

[26] S. Griffiths-Jones, H. K. Saini, S. van Dongen, A. J. Enright, *Nucleic Acids Res.* 2008, 36, D154-D158.

[27] M. Krishnamurthy, K. Simon, A. M. Orendt, P. A. Beal Angew. *Chem.* 2007, 119, 7174-7177; *Angew. Chem., Int. Ed.* 2007, 46, 7044-7047; B. D. Gooch, P. A. Beal *J. Am. Chem. Soc.* 2004, 126, 10603-10610.

[28] Shields, George C., Charles A. Laughton, and Modesto Orozco. "Molecular Dynamics Simulation of a PNA•DNA•PNA Triple Helix in Aqueous Solution." *Journal of the American Chemical Society* 120.24 (1998): 5895-5904.

[29] Shields, George C., Charles A. Laughton, and Modesto Orozco. "Molecular Dynamics Simulations of the d (T•A•T) Triple Helix." *Journal of the American Chemical Society* 119.32 (1997): 7463-7469.

[30] Praseuth, D., A. L. Guieysse, and C. Helene. "Triple helix formation and the antigene strategy for sequence-specific control of gene expression." *Biochimica et Biophysics Acta(BBA)-Gene Structure and Expression* 1489.1 (1999): 181-206.

[31] Sun, Jian-sheng, Thérèse Carestier, and Claude Hélène. "Oligonucleotide directed triple helix formation." *Current opinion in structural biology* 6.3 (1996): 327-333.

[32] Nielsen, Peter E., Michael Egholm, and Ole Buchardt. "Evidence for (PNA) 2/DNA triplex structure upon binding of PNA to dsDNA by strand displacement." *Journal of Molecular*

[33] Nielsen, Peter E., Michael Egholm, and Ole Buchardt. "Peptide nucleic acid (PNA). A DNA mimic with a peptide backbone." *Bioconjugate chemistry* 5.1 (1994): 3-7. Recognition 7.3 (2004): 165-170.

[34] Nielsen, Peter E., et al. "Sequence specific inhibition of DNA restriction enzyme cleavage by PNA." *Nucleic acids research* 21.2 (1993): 197-200.

[35] Diviacco, Silvia, et al. "Site-directed inhibition of DNA replication by triple helix formation." *The FASEB Journal* 1.5.14 (2001): 2660-2668.

[36] Casey, Brian P., and Peter M. Glazer. "Gene targeting via triple-helix formation." *Progress in nucleic acid research and molecular biology* 67 (2001): 163-192.

[37] Faruqi, A. Fawad, et al. "Triple-helix formation induces recombination in mammalian cells via a nucleotide excision repair-dependent pathway." *Molecular and cellular biology* 20.3 (2000): 990-1000.

[38] Kim, Seog K., et al. "Right-handed triplex formed between peptide nucleic acid PNA-T8 and poly (dA) shown by linear and circular dichroism spectroscopy." *Journal of the American Chemical Society* 115.15 (1993): 6477-6481.

[39] Aimarsson, Orn, and Thomas C. Bruice. "Peptide nucleic acid (PNA) conformation and polymorphism in PNA-DNA and PNA-RNA hybrids." *Proceedings of the National Academy of Sciences* 90.20 (1993): 9542-9546.

[40] Gowers, Darren M., and Keith R. Fox. "Towards mixed sequence recognition by triple helix formation." *Nucleic acids research* 27.7 (1999): 1569-1577.

[41] Uhlmann, Eugen, et al. "PNA: synthetic polyamide nucleic acids with unusual binding properties." *Angewandte Chemie International Edition* 37.20 (1998): 2796-2823.

[42] Rusling, David A., Tom Brown, and Keith R. Fox. "DNA Recognition by Triple Helix Formation." *Sequence-specific DNA Binding Agents* (2006): 1-27.

[43] Leumann, Christian J. "Design and evaluation of oligonucleotide analogues." *CHIMIA International Journal for Chemistry* 55.4 (2001): 295-301.

[44] Froehler, Brian, et al. "Enhanced triple-helix and double-helix formation with oligomers containing modified pyrimidines." U.S. Pat. No. 6,875,593. 5 Apr. 2005.

[45] Asseline, Ulysse. "Chemical Modifications of Triple Helix Forming Oligonucleotides." *Triple Helix Forming Oligonucleotides* (1999): 63-73.

[46] Szostak, Jack W. "NON-ENZYMATIC RNA REPLICATION AND THE ORIGIN OF LIFE." *Biol* 74 (2009): 47-54.

[47] Fox, Keith R, and Torn Brown. "Formation of stable DNA triplexes." *Biochemical Society Transactions* 39.2 (2011): 629.

[48], [49], [50] reserved.

[51] Thomas, J. R., and Hergenrother, P. J. (2008) Targeting RNA with Small Molecules, Chem. Rev. 108, 1171-1224.

[52] Sucheck, S. J., and Wong, C. H. (2000) RNA as a target for small molecules. Curr. Opin. Chem. Biol. 4, 678-686.

[53] Chow, C. S., and Bogdan, F. M. (1997) A Structural Basis for RNA-Ligand Interactions. Chem. Rev. 97, 1489-1513.

[54] Fox, K. R., and Brown, T. (2005) An extra dimension in nucleic acid sequence recognition. Q. Rev. Biophys. 38, 311-320.

[55] Roberts, R. W., and Crothers, D. M. (1992) Stability and properties of double and triple helices: Dramatic effects of RNA or DNA backbone composition. Science 258, 1463-1466.

[56] Han, H., and Dervan, P. B. (1993) Sequence-specific recognition of double helical RNA and RNA-DNA by triple helix formation. Proc. Natl. Acad. Sci. U.S.A. 90, 3806-3810.

[57] Escude, C., Francois, J. C., Sun, J. S., Ott, G., Sprinzl, M., Garestier, T., and Helene, C. (1993) Stability of triple helixes containing RNA and DNA strands: Experimental and molecular modeling studies. Nucleic Acids Res. 21, 5547-5553.

[58] Semerad, C. L., and Maher, L. J. (1994) Exclusion of RNA strands from a purine motif triple helix. Nucleic Acids Res. 22, 5321-5325.

[59] Nielsen, P. E., Egholm, M., Berg, R. H., and Buchardt, O. (1991) Sequence-selective recognition of DNA by strand displacement with a thymine-substituted polyamide. Science 254, 1497-1500,

[60] Li, M., Zengeya, T., and Rozners, E. (2010) Short Peptide Nucleic Acids Bind Strongly to Homopurine Tract of Double Helical RNA at pH 5.5. J. Am. Chem. Soc. 132, 8676-8681.

[61] Zengeya, T., Li, M., and Rozners, E. (2011) PNA containing isocytidine nucleobase: Synthesis and recognition of double helical RNA. Bioorg. Med. Chem. Lett. 21, 2121-2124.

[62] Gupta, Zengeya, T., and Rozners, E. (2011) Triple helical recognition of pyrimidine inversions in polypurine tracts of RNA by nucleobase-modified PNA. Chem. Commun. 47, 11125-11127.

[63] Nielsen, P. E. (2010) Sequence-selective targeting of duplex DNA by peptide nucleic acids. Curr. Opin. Mol. Ther. 12, 184-191.

[64] Shiraishi, T., and Nielsen, P. E. (2006) Enhanced delivery of cell-penetrating peptide-peptide nucleic acid conjugates by endosomal disruption. Nat. Protoc. 1, 633-636.

[65] Nielsen, P. E. (2005) Addressing the challenges of cellular delivery and bioavailability of peptide nucleic acids (PNA). Q. Rev. Biotech. 38, 345-350.

[66] Zhou, P., Dragulescu-Andrasi, A., Bhattacharya, B., O'Keefe, H., Vatta, P., Hyldig-Nielsen, J. J., and Ly, D. H. (2006) Synthesis of cellpermeable peptide nucleic acids and characterization of their hybridization and uptake properties. Bioorg. Med. Chem. Lett. 16, 4931-4935.

[67] Dragulescu-Andrasi, A., Zhou, P., He, G., and Ly, D. H. (2005) Cell-permeable GPNA with appropriate backbone stereochemistry and spacing binds sequence-specifically to RNA. Chem. Commun., 244-246.

[68] Zhou, P., Wang, M., Du, L., Fisher, G. W., Waggoner, A., and Ly, D. H. (2003) Novel Binding and Efficient Cellular Uptake of Guanidine-Based Peptide Nucleic Acids (GPNA). J. Am. Chem. Soc. 125, 6878-6879.

[69] Bradrick, T. D., and Marino, J. P. (2004) Ligand-induced changes in 2-aminopurine fluorescence as a probe for small molecule binding to HIV-1 TAR RNA, RNA 10, 1459-1468.

[70] Wojciechowski, F., and Hudson, R. H. E. (2008) A Convenient Route to N-[2-(Fmoc)aminoethyl]glycine Esters and PNA Oligomerization Using a Bis-N-Boc Nucleobase Protecting Group Strategy. J. Org. Chem. 73, 3807-3816.

[71] Kleiner, R. E., Brudno, Y., Birnbaum, M. E., and Liu, D. R. (2008) DNA-Templated Polymerization of Side-Chain-Functionalized Peptide Nucleic Acid Aldehydes. J. Am. Chem. Soc. 130, 4646-4659.

[72] Wittung, P., Nielsen, P., and Norden, B. (1996) Direct Observation of Strand Invasion by Peptide Nucleic Acid (PNA) into Double-Stranded DNA. J. Am. Chem. Soc. 118, 7049-7054.

[73] Wittung, P., Nielsen, P., and Norden, B. (1997) Extended DNA-recognition repertoire of peptide nucleic acid (PNA): PNA-dsDNA triplex formed with cytosine-rich homopyrimidine PNA. Biochemistry 36, 7973-7979.

[74] Kaushik, N., Basu, A., Palumbo, P., Myers, R. L., and Pandey, V. N. (2002) Anti-TAR polyamide nucleotide analog conjugated with a membrane-permeating peptide inhibits human immunodeficiency virus type 1 production. J. Virol. 76, 3881-3891.

[75] Tripathi, S., Chaubey, B., Ganguly, S., Harris, D., Casale, R. A., and Pandey, V. N. (2005) Anti-HIV-1 activity of anti-TAR polyamide nucleic acid conjugated with various membrane transducing peptides. Nucleic Acids Res. 33, 4345-4356.

[76] Mayhood, T., Kaushik, N., Pandey, P. K., Kashanchi, F., Deng, L., and Pandey, V. N. (2000) Inhibition of Tat-Mediated Transactivation of HIV-1 LTR Transcription by Polyamide Nucleic Acid Targeted to TAR Hairpin Element. Biochemistry 39, 11532-11539.

[77] Belousoff, M. J., Gasser, G., Graham, B., Tor, Y., and Spiccia, L. (2009) Binding of HIV-1 TAR mRNA to a peptide nucleic acid oligomer and its conjugates with metal-ion-binding multidentate ligands. J. Biol. Inorg. Chem. 14, 287-300.

[78] Lacourciere, K. A., Stivers, J. T., and Marino, J. P. (2000) Mechanism of Neomycin and Rev Peptide Binding to the Rev Responsive Element of HIV-1 As Determined by Fluorescence and NMR Spectroscopy. Biochemistry 39, 5630-5641.

[79] Kaul, M., Barbieri, C. M., and Pilch, D. S. (2004) Fluorescence-Based Approach for Detecting and Characterizing Antibiotic-Induced Conformational Changes in Ribosomal RNA: Comparing Aminoglycoside Binding to Prokaryotic and Eukaryotic Ribosomal RNA Sequences. J. Am. Chem. Soc. 126, 3447-3453.

[80] Blount, K. F., Zhao, F., Hermann, T., and Tor, Y. (2005) Conformational Constraint as a Means for Understanding RNA Aminoglycoside Specificity. J. Am. Chem. Soc. 127, 9818-9829.

[81] Hansen, M. E., Bentin, T., and Nielsen, P. E. (2009) High-affinity triplex targeting of double stranded DNA using chemically modified peptide nucleic acid oligomers. Nucleic Acids Res. 37, 4498-4507.

[82] Dragulescu-Andrasi, A., Rapireddy, S., He, G., Bhattacharya, B., Hyldig-Nielsen, J. J., Zon, G., and Ly, D. H. (2006) Cell-Permeable Peptide Nucleic Acid Designed to Bind to the 5'-Untranslated Region of E-cadherin Transcript Induces Potent and Sequence-Specific Antisense Effects. J. Am. Chem. Soc. 128, 16104-16112.

[83] Englund, E. A., and Appella, D. H. (2007) γ-substituted peptide nucleic acids constructed from L-lysine are a versatile scaffold for multifunctional display. Angew. Chem., Int. Ed. 46, 1414-1418.

[84] Sahu, B., Chenna, V., Lathrop, K. L., Thomas, S. M., Zon, G., K. J., and Ly, D. H. (2009) Synthesis of Conformationally Preorganized and Cell-Permeable Guanidine-Based γ-Peptide Nucleic Acids (γ-GPNAs). J. Org. Chem. 74, 1509-1516.

[85] Ishizuka, T., Tedeschi, T., Corradini, R., Komiyama, M., Sforza, S., and Marchelli, R. (2009) SSB-Assisted Duplex Invasion of Preorganized PNA into Double-Stranded DNA. ChemBioChem 10, 2607-2612.

[86] He, G., Rapireddy, S., Bahal, R., Sahu, B., and Ly, D. H. (2009) Strand Invasion of Extended, Mixed-Sequence B-DNA by γ-PNAs. J. Am. Chem. Soc. 131, 12088-12090.

[87] Kaihatsu, K., Braasch, D. A., Cansizoglu, A., and Corey, D. R. (2002) Enhanced strand invasion by peptide nucleic acid-peptide conjugates. Biochemistry 41, 11118-11125.

[88] Rusling, D. A., Broughton-Head, V. J., Brown, T., and Fox, K. R. (2008) Towards the targeted modulation of gene expression by modified triplex-forming oligonucleotides. Curr. Chem. Biol. 2, 1-10.

[89] Rusling, D. A., Powers, V. E. C., Ranasinghe, R. T., Wang, Y., Osborne, S. D., Brown, T., and Fox, K. R. (2005) Four base recognition by triplex-forming oligonucleotides at physiological pH. Nucleic Acids Res. 33, 3025-3032.

[90] Buchini, S., and Leurmann, C. J. (2003) Recent improvements in antigene technology. Curr. Opin. Chem. Biol. 7, 717-726.

European Patent Application no. EP2010056408.

U.S. Pat. Nos. 5,539,082; 5,547,835; 5,645,985; 5,691,141; 5,714,331; 5,719,262; 5,736,336; 5,766,855; 5,786,461; 5,830,653; 5,871918; 6,132,971; 6,190,866; 6,194,144; 6,225,450; 6,238,871; 6,248,878; 6,265,380; 6,300,318; 6,357,163; 6,361,951; 6,369,227; 6,380,368; 6,395,474; 6,403,583; 6,414,112; 6,441,130; 6,451,968; 6,500,855; 6,613,873; 6,617,309; 6,653,295; 6,664,373; 6,686,442; 6,710,058; 6,710,163; 6,710,164; 6,713,602; 6,734,161; 6,875,593; 6,878,805; 6,936,418; 6,946,292; 6,951,872; 6,962,783; 7,038,037; 7,049,068; 7,057,027; 7,098,192; 7,157,470; 7,199,107; 7,223,833; 7,235,653; 7,253,180; 7,276,599; 7,297,494; 7,307,069; 7,312,214; 7,339,051; 7,348,418; 7,368,560; 7,378,485; 7,381,732; 7,388,017; 7,390,882; 7,393,683; 7,410,772; 7,425,446; 7,429,604; 7,432,044; 7,507,859; 7,517,659; 7,524,863; 7,5413,44; 7,547,768; 7,585,953; 7,615,529; 7,618,632; 7,622,265; 7,662,929; 7,678,895; 7,683,036; 7,691,568; 7,691,810; 7,696,345; 7,704,503; 7,713,944; 7,718,628; 7,737,325; 7,741,442; 7,749,504; 7,754,441; 7,754,450; 7,759,318; 7,759,319; 7,767,403; 7,786,292; 7,790,691; 7,803,915; 7,807,372; 7,812,149; 7,829,584; 7,846,725; 7,858,330; 7,884,086; 7,888,478; 7,897,582; 7,902,163; 7,919,612; 7,923,538; 7,939,268; 7,951,546; 7,960,355; 7,981,868; 7,985,844; 7,989,595; 7,994,290; 8,008,004; 8,012,947; 8,039,595; 8,067,175; 8,067,232; 8,084,200; 8,084,459; 8,101,185; 8,106,025; 8,110,195; 8,110,558; 8,124,745; 8,129,515; 8,133,876; 8,158,760; 8,178,506; 8,183,363; 8,193,246; 8,206,901; 8,252,756; 8,278,042, expressly incorporated by reference herein in their entirety.

US Pat. Pub. Nos. 20020032175; 20020106683; 20020146718; 20020160383; 20020183324; 20030004344; 20030064962; 20030087268; 20030105286; 20030108544; 20030115614; 20030148408; 20030152953; 20030180734; 20030228305; 20030228319; 20030236389; 20040006062; 20040006203; 20040009541; 20040009602; 20040009938; 20040014051; 20040023917; 20040033977; 20040033978; 20040034191; 20040049021; 20040059087; 20040063115; 20040063179; 20040093621; 20040101853; 20040109865; 20040110704; 20040132718; 20040142346; 20040146902; 20040147022; 20040147023; 20040147470; 20040161777; 20040161844; 20040171028; 20040171029; 20040171031; 20040171032; 20040171033; 20040171564; 20040171566; 20040171570; 20040180847; 20040185479; 20040198969; 20040203024; 20040229277; 20040235164; 20040241703; 20040242860; 20040254158; 20040254358; 20040258696; 20040259150; 20040266706; 20040266731; 20050009041; 20050014224; 20050019915; 20050026160; 20050026857; 20050031613; 20050032067; 20050032068; 20050032069; 20050037370; 20050042216; 20050042647; 20050053965; 20050053976; 20050053981; 20050059016; 20050059066; 20050064492; 20050074801; 20050074879; 20050075307; 20050080032; 20050080246; 20050100885; 20050106598; 20050106644; 20050107324; 20050107595; 20050112129; 20050112770; 20050118605; 20050119470; 20050123925; 20050142581; 20050153336; 20050164250; 20050170368; 20050202459; 20050208523; 20050226867; 20050226868; 20050226869; 20050233358; 20050238650; 20050245474; 20050260634; 20050260755; 20050261218; 20050262593; 20050272120; 20050287138; 20050287548; 20060002943; 20060009455; 20060024793; 20060046255; 20060057148; 20060063254; 20060064781; 20060073505; 20060078990; 20060078991; 20060084120; 20060089496; 20060099592; 20060140961; 20060142193; 20060142232; 20060147373; 20060147374; 20060160731; 20060160997; 20060210570; 20060216232; 20060217339; 20060241071; 20060241072; 20060247243; 20060251662; 20060252722; 20060257930; 20060270594; 20060281680; 20060293269; 20070010009; 20070015722; 20070041983; 20070048218; 20070048326; 20070048825; 20070049547; 20070053835; 20070054361; 20070054869; 20070065861; 20070065862; 20070087006; 20070098634; 20070117124; 20070135364; 20070148165; 20070161547; 20070207142; 20070212735; 20070219122; 20070219350; 20070224201; 20070225282; 20070231323; 20070243193; 20070259830; 20070265436; 20070269446; 20070276139; 20070286856; 20080009456; 20080027019; 20080039618; 20080051359; 20080095765; 20080096215; 20080102468; 20080119470; 20080124331; 20080124732; 20080124739; 20080131920; 20080146495; 20080146788; 20080166294; 20080193446; 20080194503; 20080199960; 20080207541; 20080213266; 20080227106; 20080227196; 20080241130; 20080241884; 20080261301; 20080261904; 20080274993; 20080306016; 20080306153; 20080311669; 20080318239; 20090004186; 20090017473; 20090028877; 20090041749; 20090048435; 20090053226; 20090054631; 20090068178; 20090068251; 20090075278; 20090075279; 20090075302; 20090075317; 20090081660; 20090117566; 20090136928; 20090142259; 20090142806; 20090143312; 20090186363; 20090186409; 20090191199; 20090191592; 20090203132; 20090203896; 20090209629; 20090221095; 20090221685;

| | | | | | |
|---|---|---|---|---|---|
|20090228994;|20090238811;|20090246129;|20110045005;|20110052610;|20110054003;|
|20090258931;|20090286969;|20090291906;|20110059115;|20110070243;|20110124591;|
|20090291907;|20090297531;|20090298174;|20110129457;|20110137016;|20110171176;|
|20090298910;|20090311259;|20090317907;|20110171287;|20110177103;|20110178157;|
|20090324490;|20090324592;|20100028337;|20110206658;|20110206702;|20110224277;|
|20100028559;|20100061996;|20100076183;|20110236374;|20110237522;|20110240064;|
|20100080809;|20100092997;|20100113350;|20110250626;|20110250643;|20110251258;|
|20100113523;|20100113608;|20100129808;|20110262406;|20110263514;|20110268657;|
|20100136682;|20100143388;|20100158896;|20110268810;|20110274690;|20110293585;|
|20100158914;|20100162418;|20100172882;|20120009193;|20120010387;|20120022238;|
|20100173285;|20100184844;|20100209956;|20120029049;|20120035248;|20120039893;|
|20100210745;|20100216982;|20100233146;|20120052110;|20120059046;|20120077201;|
|20100233270;|20100234579;|20100240738;|20120097194;|20120114673;|20120115136;|
|20100247430;|20100249215;|20100256038;|20120115228;|20120122216;|20120142754;|
|20100267813;|20100303834;|20100311050;|20120156138;|20120157514;|20120171279;|
|20100322897;|20110009600;|20110027271;|20120184724;|20120202874;|20120244230;|
|20110033451;|20110038849;|20110042260;|20120269730, expressly incorporated by reference herein in their entirety.| | |

What is claimed is:

1. A peptide nucleic acid, comprising:
a polypeptide comprising a series of N-(2-aminoethyl)-glycines,
each N-(2-aminoethyl)-glycine being ligated to a respective Base,

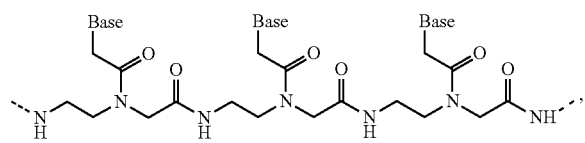

and
wherein at least one of the respective Bases is 2-aminopyridine:

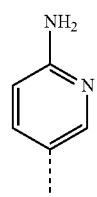

such that at least one N-(2-aminoethyl)-glycine ligated to a Base is 2-aminopyridine-ligated to a N-(2-aminoethyl)-glycine:

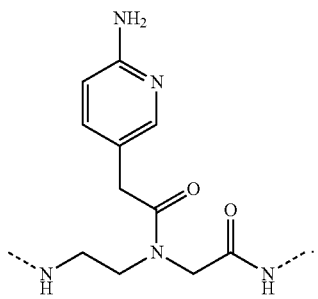

further comprising at least one basic amino acid ligated to the polypeptide.

2. The peptide nucleic acid according to claim 1, wherein the at least one basic amino acid comprises at least one terminal lysine ligated to the polypeptide.

3. The peptide nucleic acid according to claim 1, wherein at least four bases are 2-aminopyridine.

4. The peptide nucleic acid according to claim 1, wherein at least two sequential bases are 2-aminopyridine.

5. The peptide nucleic acid according to claim 1, wherein the polypeptide comprises at least six sequential base-ligated N-(2-aminoethyl)-glycines.

6. The peptide nucleic acid according to claim 1, in combination with a double stranded RNA, wherein the peptide nucleic acid forms a base sequence selective triple helix with the double stranded RNA substantially without strand invasion.

7. The peptide nucleic acid according to claim 1, wherein the peptide nucleic acid is configured to form a triple helix with a double stranded RNA having a corresponding base sequence with the peptide nucleic acid, substantially without strand invasion, which is stable at pH 7.4.

8. The peptide nucleic acid according to claim 7, wherein the peptide nucleic acid is configured to form the triple helix with the double stranded RNA, in a base sequence-selective manner at pH 7.4 at a temperature of 37° C. in an aqueous buffer comprising 2 mM $MgCl_2$, 90-mM KCl, 10 mM NaCl, and 50 mM potassium phosphate.

9. A peptide nucleic acid (PNA), comprising:
a polypeptide comprising a series of at least six N-(2-aminoethyl)-glycines,
each N-(2-aminoethyl)-glycine being ligated to a respective Base,

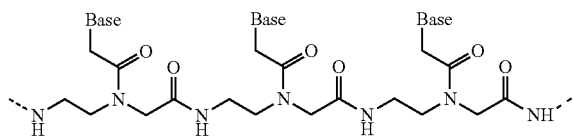

wherein at least one respective Base comprises 2-aminopyridine,
further comprising at least one basic amino acid ligated to the polypeptide.

10. The peptide nucleic acid according to claim 9, wherein the at least one basic amino acid ligated to the polypeptide comprises lysine.

11. The peptide nucleic acid according to claim 9, wherein at least two bases are 2-aminopyridine Bases.

12. The peptide nucleic acid according to claim 9, wherein the polypeptide comprises at least six sequential base-ligated N-(2-aminoethyl)-glycines.

13. The peptide nucleic acid according to claim 9, in combination with a double stranded RNA, wherein the peptide nucleic acid forms a base sequence-selective triple helix with the double stranded RNA.

14. A peptide nucleic acid (PNA), comprising a polypeptide comprising a series of N-(2-aminoethyl)-glycines, each N-(2-aminoethyl)-glycine being ligated to a respective base, wherein at least one respective base comprises 2-aminopyridine, configured to form a triple helix in sequence-selective manner with a double stranded ribonucleic acid which is stable at 37° C. in a pH 7.4 aqueous buffer comprising 2 mM $MgCl_2$, 90-mM KCl, 10 mM NaCl, and 50 mM potassium phosphate.

15. The peptide nucleic acid according to claim 14, configured to form, in combination with a double stranded RNA, a base sequence selective triple helix with the double stranded RNA substantially without strand invasion.

16. The peptide nucleic acid according to claim 14, wherein at least one N-(2-aminoethyl)-glycine ligated to the respective base comprises:

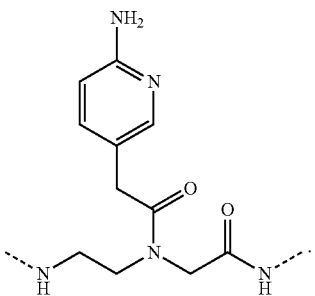

17. The peptide nucleic acid according to claim 14, further comprising at least one amino acid ligated to the series of N-(2-aminoethyl)-glycines.

18. The peptide nucleic acid according to claim 17, wherein the at least one amino acid comprises lysine.

19. The peptide nucleic acid according to claim 9, wherein at least one N-(2-aminoethyl)-glycine ligated to the respective Base comprises:

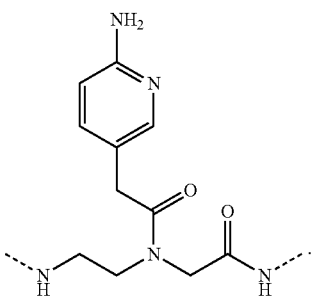

* * * * *